United States Patent [19]

Ohno et al.

[11] 4,446,325

[45] May 1, 1984

[54] 1,4-DIHYDROPYRIDINE COMPOUNDS

[75] Inventors: Sachio Ohno; Kiyoshi Mizukoshi; Osamu Komatsu, all of Aichi; Kenzi Ichihara, Gifu; Takashi Morishima, Aichi, all of Japan

[73] Assignee: Maruko Seiyaku Co., Ltd., Nagoya, Japan

[21] Appl. No.: 435,183

[22] Filed: Oct. 19, 1982

[30] Foreign Application Priority Data

Oct. 19, 1981 [JP] Japan ................................. 56-166963
Jan. 11, 1982 [JP] Japan ................................. 57-2597
Feb. 25, 1982 [JP] Japan ................................. 57-28391

[51] Int. Cl.$^3$ ................. C07D 213/55; C07D 405/12; C07D 409/12
[52] U.S. Cl. ................................. 546/283; 546/284; 546/321; 424/266

[58] Field of Search ................. 546/321, 283, 284; 424/266

[56] References Cited

U.S. PATENT DOCUMENTS 3,485,847 12/1969 Bossert et al. ................. 546/321

OTHER PUBLICATIONS

Ohno et al., Chemical Abstracts, vol. 99, No. 11, Abst. No. 99:88,063a, Sep. 12, 1983.

*Primary Examiner*—Alan L. Rotman
*Attorney, Agent, or Firm*—Sughrue, Mion, Zinn, Macpeak, and Seas

[57] ABSTRACT

1,4-Dihydropyridine compounds having excellent coronary and vertebral vasodilation, blood pressure depression and anti-hypertensive activities are disclosed. These compounds are low toxic and stable to light, and are very useful for pharmaceutical agents.

9 Claims, No Drawings

1,4-DIHYDROPYRIDINE COMPOUNDS

FIELD OF THE INVENTION

This invention relates to 1,4-dihydropyridine compounds having excellent coronary and vertebral vasodilation, blood pressure depression and antihypertensive activities. More particularly, the present invention relates to 1,4-dihydropyridine compounds represented by the formula (I)

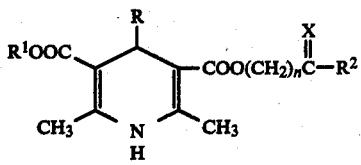

wherein R represents a 2- or 3-nitrophenyl group, $R^1$ represents a straight or branched chain alkyl group having 1 to 4 carbon atoms, $R^2$ represents hydrogen or a methyl group, X represents an oxygen atom, an ethylenedioxy group, a propylenedioxy group, an ethylenedithio group, a propylenedithio group or an ethylene group, and n is an integer of 1 or 2.

BACKGROUND OF THE INVENTION

Hitherto, it was known that 2,6-dimethyl-4-phenyl-1,4-dihydropyridine-3,5-dicarboxylate compounds exhibit interesting pharmacological activities such as vasodilation and blood pressure lowering activities as disclosed in, for example, Naturwissenschaften, 58, 578 (1972); J. Pharm. Pharmacol., 24, 917 (1972); Arnzeim.-Forsch., 22, 1 (1971); Arzneim.-Forsch., 30, 2144 (1980); J. Pharm. Sci., 62, 580 (1973); J. Med. Chem., 17, 956 (1974); Belgian Patent No. 689,377; U.S. Pat. No. 3,485,847. Of these known compounds, dimethyl 2,6-dimethyl-4-(2-nitrophenyl)-1,4-dihydropyridine-3,5-dicarboxylate disclosed in the above U.S. Pat. No. 3,485,847 is now commercially available under the general name of "nifedipine" as a coronary vasodialtor. However, nifedipine is still unsatisfactory in the duration of its vasodilating activity and its side-effects.

Further nifedipine is extremely unstable to light and such defect causes various problems in preparing pharmaceutical preparations containing nifedipine, as reported in Kiso To Rinsho (Tokyo), 6, 259 (1972); Arzneim.-Forsch., 28, 2188 (1978); Yakugaku Zasshi, 101, 1149 (1981), etc.

Under such circumstances, various attempts have been made to develop 1,4-dihydropyridine-3,5-dicarboxylate derivatives having higher pharmacological activities and light-stability and lower side-effects and such derivatives have been proposed in, for examples, German OLS Nos. 2,747,513, 2,841,667, 2,847,237, 2,921,429, 2,847,236, 1,963,188, 1,923,990, 2,117,571, 2,117,573, 2,005,116, 2,218,644 and 2,549,568; and Japanese Patent Publication (Unexamined) Nos. 84576/75, 101365/75, 131970/75, 40576/75, 12632/76, 95976/78, 9083/80, 40678/80, 127356/81, etc.

However, most of the compounds disclosed in the above prior art references would still require further improvements in their pharmacological activities, absorption from gastro-intestinal tracts, side-effects, toxicity and/or light-stability.

As a result of extensive studies to overcome the disadvantages of these known 1,4-dihydropyridine compounds, the present inventors found that the 1,4-dihydropyridine compounds represented by the formula (I) above exhibit markedly excellent properties in every aspects and completed the present invention.

Surprisingly, the 1,4-dihydropyridine compounds of the formula (I) according to the present invention possess markedly strong coronary and vertebral artery vasodilating activity, blood pressure lowering activity and antihypertensive activity and, hence, they are useful as pharmaceutical agent for prevention and treatment of ischemic cardiac failure, cerebral circulation disturbance, hypertension and/or the complication of these disorders. In addition, these compounds are of low toxicity and stable to light.

It was also known that 2,6-dimethyl-4-phenyl-1,4-dihydropyridine-3,5-dicarboxylate derivatives can be prepared by a so-called Hantzsch reaction or modifications thereof, i.e., by the reaction between a benzylidineacetoacetate derivative and a β-aminocrotonate derivative or between benzylideneacetoacetate, an acetoacetate derivative and ammonia as disclosed in, for example, Ann., 215, 1 (1882), Ber., 15, 2914 (1882); ibid, 17, 1521 (1884); ibid, 17, 2903 (1884); ibid, 20, 1338 (1887); ibid, 31, 743 (1898); J. Chem. Soc., 413 (1943); J. Amer. Shem. Soc., 71, 4003 (1949); J. Org. Chem., 30, 1914 (1965). The 1,4-dihydropyridine compounds of the formula (I) can also be prepared easily according to a conventional procedure from commercially available starting materials as hereinafter described in detail.

DETAIL DESCRIPTION OF THE INVENTION

The 1,4-dihydropyridine compounds of the formula (I) can be prepared by the following alternative procedures.

The compounds of the formula (I) wherein X is an ethylenedioxy group, a propylenedioxy group, an ethylenedithio group, a propylenedithio group or an ethylene group can be prepared by reacting a benzlidene acetoacetate compound represented by the formula (II)

wherein R represents a 2- or 3-nitrophenyl group and $R^1$ represents a straight or branched chain alkyl group having 1 to 4 carbon atoms, with an aminocrotonate represented by the formula (III)

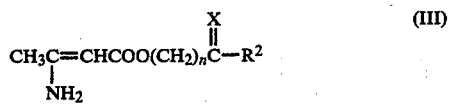

wherein $R^2$ represents hydrogen or a methyl group, X represents the group as defined above other than the oxygen atom and n is an integer of 1 or 2, in an inert organic solvent, for example, an alkanol having 1 to 4 carbon atoms such as methanol, ethanol, isopropanol, butanol and the like, at a temperature of from about 50° C. to about 150° C. for a period of about 1 to about 20 hours using an equimolar amount of the reactants of the formulae (II) and (III).

The compounds of the formula (I) wherein X represents the group as defined above other than the oxygne atom can also be prepared by reacting 2- or 3-nitrobenzaldehyde, an aminocrotonate represented by the formula (IV)

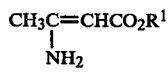 (IV)

wherein $R^1$ is as defined above, and an acetoacetate represented by the formula (V)

 (V)

wherein $R^2$ is as defined above and X represents the group as defined above other than the oxygen atom, at a temperature of about 50° to about 150° C. for a period of about 1 to about 20 hours at a molar ratio of about 1:1 of the benzaldehyde:the aminocrotonate (IV), and a slightly molar excess of the acetoacetate, for example, a molar ratio of about 0.7:0.7:1 of benzaldehyde:aminocrotonate (IV):acetoacetate (V).

The compounds of the formula (I) wherein X is the group as defined above other than the oxygen atom can also be prepared by reacting benzylideneacetoacetate represented by the formula (VI)

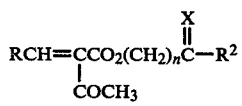 (VI)

wherein R and $R^2$ are as defined above and X represents the group as defined above other than the oxygen atom, with an aminocrotonate represented by the formula (IV) above, at an approximately equimolar proportion in an organic solvent such as methanol, ethanol, isopropyl alcohol, isopropyl ether, etc. at a temperature of about 50° to about 10° C. for a period of about 2 to about 10 hours.

The compounds of the formula (I) wherein X represents an oxygen atom can be prepared by treating a compound of the formula (I) wherein X represents an ethylenedioxy group or a propylenedioxy group, in an aqueous medium, for example, a mixed solvent system comprising water and methanol, ethanol, isopropanol, acetone or the like, containing an acid such as hydrochloric acid, sulfuric acid and the like at a concentration of about 10 wt.%, at a temperature of about 50° to about 100° C. for a period of about 1 to about 10 hours.

Alternatively, the compounds of the formula (I) wherein X represents an ethylenedioxy group, a propylenedioxy group, an ethylenedithio group or a propylenedithio group, can be prepared by reacting a compound of the formula (I) wherein X represents an oxygen atom, with 1,2-ethanediol, 1,3-propanediol, 1,2-ethanedithiol or 1,3-propanedithiol in the presence of an acid such as p-toluenesulfonic acid, boron trifluoride, etc., at a temperature of about 0° C. to about 150° C. for a period of about 1 to about 24 hours, at a molar ratio of about 3 to about 10 moles of the diol or the dithiol per mole of the compound of the formula (I) (X=O).

Some of the compounds of the formula (II) used as starting materials are novel compounds and these novel compounds can be prepared easily by a conventional procedure as described in, for example, Organic Reactions XV, 204 (1967) as illustrated below:

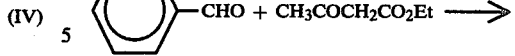

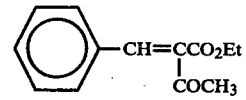

The aminocrotonate of the formula (III) above used as starting material can be prepared by passing an ammonia gas into a solution of a known acetoacetate compound of the formula (V) in a solvent such as methanol, ethanol, diethyl ether, dioxane and the like, while cooling, e.g., under ice-cooling condition.

Other starting materials, i.e., aminocrotonates of the formula (IV) and benzylideneacetoacetates of the formula (VI) can be prepared by the method described above.

The compounds of the present invention having the formula (I) can be administered orally, intrarectally or parenterally, alone or in admixture with other pharmaceutical carriers, excipients, binders, lubricants and the like, in dosage forms such as tablets, trochs, pills, granules, powders, capsules, ampule preparations, suppositories, and the like. Examples of suitable carriers, excipients, binders, lublicants, etc. for formulating into the above dosage forms include starch, dextrin, sucrose, lactose, silicic acid, carboxymethyl cellulose, cellulose, gelatin, polyvinyl pyrrolidone, glycerin, agar, calcium carbonate, sodium bicarbonate, paraffin, cetyl alcohol, stearic acid ester, kaolin, bentonite, talc, potassium stearate, magnesium stearate, polyethylene glycol, water ethanol, isopropyl alcohol, propylene glycol and the like.

The dosage level of the compounds of the formula (I) by oral administration is usually in the range of from about 0.005 to about 20 mg/kg of body weight per day, but the dosage level can, of course, be reduced or increased appropriately depending upon the severity of conditions to be treated, the age of patients and other various factors.

The present invention is further illustrated in greater detail by the following Reference Examples and Examples.

REFERENCE EXAMPLE 1

100 mg of 50% sodium hydride was added to a mixture of 20 g of 2,2-ethylenedioxypropanol and 100 ml of benzene, and 20 g of diketene was added dropwise to the mixture while refluxing the mixture. After refluxing the mixture for 2 hours, the solvent was distilled off and the resulting residue was distilled under reduced pressure to obtain 21.5 g (70% yield) of 2,2-ethylenedioxypropyl acetoacetate as a colorless oil having a boiling point of 90° C. (6 mmHg).

NMR (CDCl$_3$) δ: 1.40 (3H, s), 2.30 (3H, s), 3.50 (2H, s), 3.99 (4H, s), 4.01 (2H, s).

REFERENCE EXAMPLE 2

Ammonia gas was passed through a mixture of 19 g of 2,2-ethylenedioxypropyl acetoacetate and 100 ml of methanol for 2.5 hours under ice-cooling while stirring. The solvent was then distilled off and the residue was distilled under reduced pressure to obtain 16 g (84% yield) of 2,2-ethylenedioxypropyl 3-aminocrotonate as a pale yellow oil having a boiling point of 120° C. (5 mmHg).

NMR (CDCl$_3$) δ: 1.43 (3H, s), 1.97 (3H, s), 4.00 (4H, s), 4.03 (2H, s), 4.57 (1H, s like), 6.50 (1H, br)

The following compounds (Reference Examples 3 and 4) as starting materials were prepared in the same manner as described in Reference Examples 1 and 2.

REFERENCE EXAMPLE 3

3,3-Ethylenedioxybutyl acetoacetate as a colorless oil having a boiling point of 120° C. (5 mmHg).

NMR (CDCl$_3$) δ: 1.33 (3H, s), 2.05 (2H, t, J=7.0 Hz), 2.60 (3H, s), 3.53 (2H, s), 3.98 (4H, s), 4.30 (2H, t, J=7.0 Hz)

REFERENCE EXAMPLE 4

3,3-Ethylenedioxybutyl 3-aminocrotonate as a pale yellow oil having a boiling point of 144° C. (4 mmHg).

NMR (CDCl$_3$) δ: 1.40 (3H, s), 1.93 (3H, s), 2.04 (2H, t, J=7.0 Hz), 3.94 (4H, s), 4.16 (2H, t, J=7.0 Hz), 4.46 (1H, s like), 6.50 (2H, br)

REFERENCE EXAMPLE 5

0.1 g of sodium hydride (50%) was added to 25 g of cyclopropylmethanol and then 29 g of diketene was added dropwise thereto at a temperature of 50° to 60° C. with stirring. After completion of the addition, the mixture was heated at that temperature for 1 hour. The resulting oil was distilled under reduced pressure to obtain 50 g (93% yield) of cyclopropylmethyl acetoacetate as a colorless oil having a boiling point of 78° C. (4 mmHg).

NMR (CDCl$_3$): 0.13–0.74 (4H, m), 1.16 (1H, m), 2.28 (3H, s), 3.50 (2H, s), 3.99 (2H, d, J=7.5 Hz)

REFERENCE EXAMPLE 6

21 g of cyclopropylmethyl acetoacetate was dissolved in 100 ml of methanol and ammonia gas was bubbled into the solution for 5 hours under ice-cooling. The solvent was then distilled off to obtain crystals which were then recrystallized from hexane to obtain 17.8 g (85% yield) of cyclopropylmethyl 3-aminocrotonate as colorless needles having a melting point of 55°–58° C.

NMR (CDCl$_3$) δ: 0.15–0.73 (4H, m), 0.82–1.40 (1H, m), 1.90 (3H, s), 4.90 (2H, d, J=6.7 Hz), 3.55 (1H, s), 6.37 (2H, br)

EXAMPLE 1

A mixture of 10 g of methyl 3'-nitrobenzylidene acetoacetate, 7.5 g of 2,2-ethylenedioxypropyl 3-aminocrotonate and 120 ml of ethanol was refluxed for 10 hours. The resulting reaction solution was allowed to stand overnight, and the precipitated crystals were collected by filtration and recrystallized from ethanol to obtain 11.0 g (63% yield) of methyl 2,2-ethylenedioxypropyl 2,6-dimethyl-4-(3-nitrophenyl)-1,4-dihydropyridine-3,5-dicarboxylate as yellow needles having a melting point of 143° C.

NMR (CDCl$_3$) δ: 1.22 (3H, s), 2.29 (6H, s), 3.59 (3H, s), 3.90 (4H, s), 3.98 (2H, s), 5.11 (1H, s), 6.48 (1H, br s), 7.23–8.20 (4H, m)

EXAMPLE 2

8.2 g of methyl 2,2-ethylenedioxypropyl 2,6-dimethyl-4-(3-nitrophenyl)-1,4-dihydropyridine-3,5-dicarboxylate was refluxed in 35 ml of an ethanol solution containing 5 ml of 10% hydrochloric acid for 6 hours. The solvent was then distilled off and the residue was crystallized from diethyl ether. Recrystallization of the crystals from a mixture of ethyl acetate and hexane gave 4.8 g (65% yield) of methyl 2-oxopropyl 2,6-dimethyl-4-(3-nitrophenyl)-1,4-dihydropyridine-3,5-dicarboxylate as yellow prisms having a melting point of 139° C.

NMR (CDCl$_3$) δ: 2.10 (3H, s), 2.37 (6H, s), 3.67 (3H, s), 4.67 (2H, s), 5.17 (1H, s), 7.03–8.23 (5H, m)

EXAMPLE 3

A mixture of 15 g of ethyl 2-nitrobenzylideneacetoacetate, 13 g of 3-aminocrotonate and 100 ml of ethanol was refluxed for 8 hours. The solvent was then distilled off and the resulting oil was purified by silica gel chromatography using diethyl ether as an eluant to obtain 19.5 g (77% yield) of ethyl 2,2-ethylenedioxypropyl 2,6-dimethyl-4-(2-nitrophenyl)-1,4-dihydropyridine-3,5-dicarboxylate as a yellow oil.

NMR (CDCl$_3$) δ: 1.15 (3H, t, J=7.1 Hz), 1.26 (3H, s), 2.30 (6H, s), 3.77–4.33 (4H, m), 3.88 (4H, s), 5.81 (1H, s), 6.26 (1H, br s), 7.00–7.80 (4H, m)

The following compounds (Examples 4 to 18) were also prepared in the same manner as described in Examples 1 to 3.

EXAMPLE 4

Methyl 2,2-ethylenedioxypropyl 2,6-dimethyl-4-(2-nitrophenyl)-1,4-dihydropyridine-3,5-dicarboxylate. Recrystallized from a mixture of isopropyl alcohol and hexane. Yellow prisms, melting point: 156° C.

EXAMPLE 5

Methyl 2-oxopropyl 2,6-dimethyl-4-(2-nitrophenyl)-1,4-dihydropyridine-3,5-dicarboxylate. Recrystallized from a mixture of ethyl acetate and hexane. Yellow prisms, melting point: 155° C.

EXAMPLE 6

Propyl 2,2-ethylenedioxypropyl 2,6-dimethyl-4-(3-nitrophenyl)-1,4-dihydropyridine-3,5-dicarboxylate. Recrystallized from a mixture of isopropyl alcohol and hexane. Yellow prisms, melting point: 115° C.

EXAMPLE 7

Ethyl 3,3-ethylenedioxybutyl 2,6-dimethyl-4-(3-nitrophenyl)-1,4-dihydropyridine-3,5-dicarboxylate. Recrystallized from a mixture of ethanol and diethyl ether. Yellow prisms, melting point: 136° C.

EXAMPLE 8

Ethyl 2,2-ethylenedioxypropyl 2,6-dimethyl-4-(3-nitrophenyl)-1,4-dihydropyridine-3,5-dicarboxylate. Recrystallized from ethanol. Yellow needles, melting point: 153° C.

EXAMPLE 9

Methyl 3,3-ethylenedioxybutyl 2,6-dimethyl-4-(2-nitrophenyl)-1,4-dihydropyridine-3,5-dicarboxylate. Yellow oil.

NMR (CDCl$_3$) δ: 1.25 (3H, s), 1.82–2.17 (2H, m), 2.26 (3H, s), 2.31 (3H, s), 3.84–4.40 (6H, m, 3.87 (4H, s)), 5.76 (1H, s), 6.20 (1H, br s), 7.06–7.85 (4H, m).

EXAMPLE 10

Isopropyl 3,3-ethylenedioxypropyl 2,6-dimethyl-4-(3-nitrophenyl)-1,4-dihydropyridine-3,5-dicarboxylate.

Recrystallized from a mixture of isopropyl alcohol and isopropyl ether. Yellow prisms, melting point: 128° C.

EXAMPLE 11

Isopropyl 2,2-ethylenedioxypropyl-2,6-dimethyl-4-(3-nitrophenyl)-1,4-dihydropyridine-3,5-dicarboxylate. Recrystallized from a mixture of ethyl acetate and hexane. Yellow needles, melting point: 126° C.

EXAMPLE 12

Isopropyl 2-oxopropyl 2,6-dimethyl-4-(3-nitrophenyl)-1,4-dihydropyridine-3,5-dicarboxylate. Yellow oil.

NMR (CDCl$_3$) δ: 1.15 (3H, d, J=6.0 Hz), 1.25 (3H, d, J=6.0 Hz), 2.05 (3H, s), 2.33 (6H, s), 4.66 (2H, s), 4.97 (1H, m), 5.13 (1H, s), 6.83 (1H, br s), 7.23–8.30 (4H, m)

EXAMPLE 13

Methyl 3-oxobutyl 2,6-dimethyl-4-(3-nitrophenyl)-1,4-dihydropyridine-3,5-dicarboxylate. Yellow oil.

NMR (CDCl$_3$) δ: 2.15 (3H, s), 2.35 (6H, s), 2.75 (2H, t, J=6.0 Hz), 3.66 (3H, s), 4.33 (2H, t, J=6.0 Hz), 5.06 (1H, s), 6.50 (1H, br s), 7.20–8.20 (4H, m)

EXAMPLE 14

Ethyl 3-oxobutyl 2,6-dimethyl-4-(3-nitrophenyl)-1,4-dihydropyrimidine-3,5-dicarboxylate. Yellow oil.

NMR (CDCl$_3$) δ: 1.20 (3H, t, J=7.0 Hz), 2.12 (3H, s), 2.32 (6H, s), 2.70 (2H, t, J=6.0 Hz), 4.08 (2H, q, J=7.0 Hz), 4.29 (2H, t, J=6.0 Hz), 5.03 (1H, s), 6.26 (1H, br s), 7.17–8.22 (4H, m)

EXAMPLE 15

Isopropyl 3-oxobutyl 2,6-dimethyl-4-(3-nitrophenyl)-1,4-dihydropyridine-3,5-dicarboxylate. Yellow oil.

NMR (CDCl$_3$) δ: 1.15 (3H, d, J=6.0 Hz), 1.30 (3H, d, J=6.0 Hz), 2.15 (3H, s), 2.35 (6H, s), 2.76 (2H, t, J=6.0 Hz), 4.31 (2H, t, J=6.0 Hz), 4.95 (1H, m), 5.05 (1H, s), 6.89 (1H, br s), 7.23–8.20 (4H, m)

EXAMPLE 16

Ethyl 2-oxopropyl 2,6-dimethyl-4-(3-nitrophenyl)-1,4-dihydropyridine-3,5-dicarboxylate. Recrystallized from isopropyl alcohol. Pale yellow needles, melting point: 156° C.

EXAMPLE 17

Propyl 2-oxopropyl 2,6-dimethyl-4-(3-nitrophenyl)-1,4-dihydropyridine-3,5-dicarboxylate. Recrystallized from a mixture of dichloromethane-diethyl ether. Pale yellow needles, melting point: 101° C.

EXAMPLE 18

Methyl 3,3-ethylenedioxybutyl 2,6-dimethyl-4-(3-nitrophenyl)-1,4-dihydropyridine-3,5-dicarboxylate. Recrystallized from a mixture of ethanol and diethyl ether. Yellow prisms, melting point: 156° C.

EXAMPLE 19

A mixture of 5 g of methyl 2-oxopropyl 2,6-dimethyl-4-(3-nitrophenyl)-1,4-dihydropyridine-3,5-dicarboxylate, 4 g of 1,3-propanediol, 50 mg of p-toluenesulfonic acid and 50 ml of benzene was refluxed under a water-trap for 20 hours. After allowing the mixture to cool, the mixture was washed with water and dried over anhydrous magnesium sulfate. The solvent was then distilled off and the oily residue was crystallized from isopropyl ether. Recrystallization from a mixture of ethanol and isopropyl ether gave 4.2 g (74% yield) of methyl 2,2-trimethylenedioxypropyl 2,6-dimethyl-4-(3-nitrophenyl)-1,4-dihydropyridine-3,5-dicarboxylate as pale yellow prisms having a melting point of 131°–134° C.

NMR (CDCl$_3$) δ: 1.33 (3H, s), 1.47–2.00 (2H, m), 2.33 (3H, s), 2.35 (3H, s), 3.27–4.30 (4H, m), 3.62 (3H, s), 4.13 (2H, s), 5.15 (1H, s), 6.78 (1H, br, s), 7.25–8.28 (4H, m)

EXAMPLE 20

A mixture of 5 g of propyl 2-oxopropyl 2,6-dimethyl-4-(3-nitrophenyl)-1,4-dihydropyridine-3,5-dicarboxylate, 5 g of 1,3-propanediol, 100 mg of methanesulfonic acid and 50 ml of benzene was refluxed under a water-trap for 20 hours. After allowing the mixture to cool, the mixture was washed with water and dried over anhydrous magnesium sulfate. The solvent was distilled off and the resulting oily residue was purified by silica gel chromatography (eluted with ethyl acetate-hexane, 1:1 by volume) to obtain 3.2 g (56% yield) of propyl 2,2-trimethylenedioxypropyl 2,6-dimethyl-4-(3-nitrophenyl)-1,4-dihydropyridine-3,5-dicarboxylate as a yellow oil.

NMR (CDCl$_3$) δ: 0.90 (3H, t, J=6.8 Hz), 1.19–1.97 (4H, m), 1.34 (3H, s), 2.36 (6H, s), 3.65–4.26 (8H, m, 4.13 (2H, s)), 5.14 (1H, s), 6.10 (1H, br s), 7.18–8.25 (4H, m)

EXAMPLE 21

4 ml of boron trifluoride etherate was added to a solution of 6 g of methyl 2-oxopropyl 2,6-dimethyl-4-(3-nitrophenyl)-1,4-dihydropyridine-3,5-dicarboxylate, 5 g of 1,2-ethylenedithiol and 50 ml of chloroformate under ice-cooling and the mixture was stirred for 3 hours under ice-cooling. After completion of the reaction, the reaction mixture was washed successively with an aqueous solution of sodium carbonate and water, and dried over anhydrous magnesium sulfate. The solvent was distilled off and the oily residue was purified by silica gel chromatography (eluted with diethyl ether). The resulting oily product was crystallized from isopropyl ether and recrystallized from a mixture of ethanol and diethyl ether to obtain 2.5 g (35% yield) of methyl 2,2-ethylenedithiopropyl 2,6-dimethyl-4-(3-nitrophenyl)-1,4-dihydropyridine-3,5-dicarboxylate as pale yellow needles having a melting point of 139°–144° C.

NMR (CDCl$_3$) δ: 1.70 (3H, s), 2.38 (3H, s), 2.43 (3H, s), 3.33 (4H, s), 3.72 (3H, s), 4.22 (2H, s), 5.20 (1H, s), 6.33 (1H, br s), 7.23–8.25 (4H, m)

The following compounds (Examples 22 to 25) were also prepared in the same manner as described in Examples 19 to 21.

EXAMPLE 22

Ethyl 2,2-trimethylenedioxypropyl 2,6-dimethyl-4-(3-nitrophenyl)-1,4-dihydropyridine-3,5-dicarboxylate. Recrystallized from a mixture of isopropyl alcohol and hexane. Pale yellow prisms, melting point: 120°–122° C.

EXAMPLE 23

Ethyl 2,2-ethylenedioxypropyl 2,6-dimethyl-4-(3-nitrophenyl)-1,4-dihydropyridine-3,5-dicarboxylate. Recrystallized from a mixture of dichloromethane and diethyl ether. Yellow needles, melting point: 143°–145° C.

EXAMPLE 24

Propyl 2,2-ethylenedioxypropyl 2,6-dimethyl-4-(3-nitrophenyl)-1,4-dihydropyridine-3,5-dicarboxylate.

Recrystallized from a mixture of dichloromethane and diethyl ether. Yellow needles, melting point: 124°–127° C.

EXAMPLE 25

Methyl 2,2-trimethylenedioxypropyl 2,6-dimethyl-4-(3-nitrophenyl)-1,4-dihydropyridine-3,5-dicarboxylate. Pale yellow oil.

NMR (CDCl$_3$) δ: 0.98 (3H, t, J=7.0 Hz), 1.23–2.20 (4H, m), 1.46 (3H, s), 2.40 (3H, s), 2.45 (3H, s), 2.55–3.13 (4H, m), 4.07 (2H, t, J=6.5 Hz), 4.26 (1H, d, J=11 Hz), 4.52 (1H, d, J=11 Hz), 5.22 (1H, s), 6.35 (1H, br s), 7.23–8.27 (4H, m)

EXAMPLE 26

A mixture of 15 g of methyl 3'-nitrobenzylideneacetoacetate, 9.4 g of cyclopropylmethyl 3-aminocrotonate and 80 ml of ethanol was refluxed for 8 hours. The solvent was then distilled off and the resulting crystals were recrystallized from a mixture of ethanol and isopropyl ether to obtain 15.2 g (65% yield) of cyclopropylmethyl methyl 2,6-dimethyl-4-(3-nitrophenyl)-1,4-dihydropyridine-3,5-dicarboxylate as pale yellow needles having a melting point of 160°–163° C.

NMR (CDCl$_3$) δ: 0.13–0.76 (4H, m), 1.13 (1H, m), 2.37 (6H, s), 3.66 (3H, s), 3.90 (2H, d, J=6.5 Hz), 5.15 (1H, s), 6.26 (1H, br s), 7.22–8.25 (4H, m)

EXAMPLE 27

A mixture of 7.0 g of cyclopropylmethyl acetoacetate, 9.0 g of 3-nitrobenzaldehyde and 80 ml of ethanol was refluxed for 8 hours. The solvent was distilled off and the resulting crystals were recrystallized from a mixture of ethanol and isopropyl ether to obtain 13.0 g (56% yield) of cyclopropylmethyl methyl 2,6-dimethyl-4-(3-nitrophenyl)-1,4-dihydropyridine-3,5-dicarboxylate as pale yellow needles having a melting point of 160°–163° C.

EXAMPLE 28

A mixture of 8.5 g of ethyl 3'-nitrobenzylideneacetoacetate, 5.0 g of cyclopropylmethyl 3-aminocrotonate and 60 ml of ethanol was refluxed for 5 hours. The solvent was then distilled off, and the residue was crystallized from isopropyl ether and then recrystallized from ethanol-isopropyl ether to obtain 7.6 g (59% yield) of cyclopropylmethyl ethyl 2,6-dimethyl-4-(3-nitrophenyl)-1,4-dihydropyridine-3,5-dicarboxylate as pale yellow needles having a melting point of 169°–170° C.

NMR (CDCl$_3$) δ: 0.12–0.68 (4H, m), 0.77–1.43 (1H, m), 1.25 (3H, t, J=7.0 Hz), 2.37 (6H, s), 3.89 (2H, d, J=6.5 Hz), 4.11 (2H, q, J=7.0 Hz), 5.15 (1H, s), 6.28 (1H, br s), 7.23–8.26 (4H, m)

EXAMPLE 29

A mixture of 8.9 g of propyl 3'-nitrobenzylideneacetoacetate, 5.0 g of cyclopropylmethyl 3-aminocrotonate and 60 ml of ethanol was refluxed for 5 hours. The solvent was distilled off and the residue was crystallized from isopropyl ether and then recrystallized from a mixture of ethanol and isopropyl ether to obtain 8.0 g (60% yield) of cyclopropylmethyl propyl 2,6-dimethyl-4-(3-nitrophenyl)-1,4-dihydropyridine-3,5-dicarboxylate as pale yellow prisms having a melting point of 167°–168° C.

NMR (CDCl$_3$) δ: 0.13–2.12 (10H, m), 2.37 (6H, s), 3.90 (2H, d, J=7.0 Hz), 4.03 (2H, q, J=6.0 Hz), 5.18 (1H, s), 6.40 (1H, br s), 7.22–8.33 (4H, m)

COMPARATIVE EXAMPLE

The pharmacological activities, toxicity and light-stability of some typical compounds of this invention having the formula (I) were tested in comparison with known compounds. The compounds used in these tests were as follows:

Compound A: Methyl 2,2-ethylenedioxypropyl 2,6-dimethyl-4-(3-nitrophenyl)-1,4-dihydropyridine-3,5-dicarboxylate (prepared in Example 1)

Compound B: Methyl 2-oxopropyl 2,6-dimethyl-4-(2-nitrophenyl)-1,4-dihydropyridine-3,5-dicarboxylate (prepared in Example 5)

Compound C: Cyclopropylmethyl methyl 2,6-dimethyl-4-(3-nitrophenyl)-1,4-dihydropyridine-3,5-dicarboxylate (prepared in Examples 26 and 27)

Compound D: Cyclopropylmethyl ethyl 2,6-dimethyl-4-(3-nitrophenyl)-1,4-dihydropyridine-3,5-dicarboxylate (prepared in Example 28)

Compound E: Cyclopropylmethyl propyl 2,6-dimethyl-4-(3-nitrophenyl)-1,4-dihydropyridine-3,5-dicarboxylate (prepared in Example 29)

Compound F: Isobutyl methyl 2,6-dimethyl-4-(2-nitrophenyl)-1,4-dicarboxylate (disclosed in German OLS No. 2,549,568)

Compound G: Dimethyl 2,6-dimethyl-4-(3-nitrophenyl)-1,4-dihydropyridine-3,5-dicarboxylate [reported in J. Amer. Chem. Soc., 71, 4003 (1949)]

Compound H: Dimethyl 2,6-dimethyl-4-(2-nitrophenyl)-1,4-dihydropyridine-3,5-dicarboxylate (general name "nifedipine" disclosed in U.S. Pat. No. 3,485,847)

Blood Flow Increasing Activity in Coronary, Vertebral and Femoral Arteris

A dog was anesthetized with pentobarital sodium at a dose of 30 mg/kg (intravenous injection) and, under artificial respiration, the blood flow in the coronary, vertebral and femoral arteries was determined using an electromagnetic blood-flow meter. The blood pressure was also measured simultaneously. The test compound was dissolved in ethanol at a concentration of 1% by weight of the compound and then diluted to a volume of 10 times with a 80% aqueous solution of polyethylene glycol 400. The resulting solution was further diluted with a 0.9% physiological saline solution and administered intravenously into the femoral vein at a dose shown in Tables 1 and 2. Two tests were conducted separately and the results obtained in these tests are shown in Tables 1 and 2, respectively.

TABLE 1

| Test Compound | Dose (mg/kg) | Total Increase in Blood Flow (ml) | | | Duration of Activity | | |
|---|---|---|---|---|---|---|---|
| | | Coronary Artery | Vertebral Artery | Femoral Artery | Coronary Artery | Vertebral Artery | Femoral Artery |
| Compound A | 1 | 22 | 64 | 104 | 5.5 | 11.7 | 9.0 |
| Compound A | 3 | 164 | 288 | 316 | 17.5 | 27.3 | 19.3 |
| Compound B | 1 | 37 | 29 | 20 | 10.0 | 7.5 | 4.0 |
| Compound B | 3 | 392 | 309 | 774 | 35.0 | 35.5 | 58.5 |

TABLE 1-continued

| Test Compound | Dose (mg/kg) | Total Increase in Blood Flow (ml) | | | Duration of Activity | | |
|---|---|---|---|---|---|---|---|
| | | Coronary Artery | Vertebral Artery | Femoral Artery | Coronary Artery | Vertebral Artery | Femoral Artery |
| Compound H | 1 | 30 | 66 | 34 | 3.9 | 8.0 | 6.0 |
| Compound H | 3 | 107 | 190 | 618 | 9.3 | 16.0 | 21.5 |

TABLE 2

| Test Compound | Dose (mg/kg) | Total Increase in Blood Flow (ml) | | | Duration of Activity | | |
|---|---|---|---|---|---|---|---|
| | | Coronary Artery | Vertebral Artery | Femoral Artery | Coronary Artery | Vertebral Artery | Femoral Artery |
| Compound C | 3 | 580 | 463 | 367 | 49 | 37 | 26 |
| Compound C | 10 | 2772 | 1691 | 811 | 66 | 78 | 60 |
| Compound D | 3 | 308 | 212 | 173 | 32 | 17 | 16 |
| Compound E | 3 | 148 | 262 | 285 | 22 | 19 | 20 |
| Compound F | 3 | 353 | 347 | 365 | 31 | 34 | 27 |
| Compound F | 10 | 863 | — | 874 | 55 | — | 58 |
| Compound G | 3 | — | 50 | 30 | — | 4 | 3 |
| Compound H | 3 | 146 | 131 | 119 | 11 | 15 | 12 |
| Compound H | 10 | 536 | 640 | 825 | 40 | 46 | 54 |

As is apparent from the results in Tables 1 and 2, each of the test compounds according to the present invention is superior to nifedipine (Compound H) in both the blood flow increasing activity in the coronary, vertebral and femoral arteries and the duration of activity. In particular, as shown in Table 2, Compound C of the present invention exhibits vasodilation effect and its duration significantly higher than those of Compound F which has been reported to have a very strong vasodilation activity (e.g., German OLS No. 2,529,568; Arzneim.-Forsch., 30, 2144 (1980); etc.). On the other hand, Compound G which as a chemical structure similar to that of Compound C but contains no cyclopropyl group exhibited only a very weak activity. Further, Compounds A to F and nifedipine were also found to have a blood pressure lowering activity.

Other closely related compounds, e.g., cyclohexyl ethyl 2,6-dimethyl-4-(3-nitrophenyl)-1,4-dihydropyridine-3,5-dicarboxylate, disclosed in German OLS Nos. 2,117,571 and 2,117,573 have been reported to have weak activities.

Effect on Enucleated Heart of Guinea-pig

The effects of the compounds of this invention on the heat systole and the perfusion volume in the coronary artery in enucleated heart of guinea-pig were determined in accordance with the Langendorf method.

The results obtained are shown in Table 3 below.

TABLE 3

| Compound | Dose (g) | Effects on Heart Systole | | Effects on Coronary Artery | |
|---|---|---|---|---|---|
| | | Changes in Systole (%) | Duration of Effect (min.) | Total Perfusion Volume (drops) | Duration of Effect (min.) |
| Compound A | $1 \times 10^{-6}$ | −32.9 | 4.6 | 737.8 | 34.6 |
| Compound A | $1 \times 10^{-7}$ | −5.3 | 1.3 | 165.0 | 15.6 |
| Compound H | $1 \times 10^{-6}$ | −56.6 | 14.5 | 192.8 | 21.3 |
| Compound H | $1 \times 10^{-7}$ | −19.8 | 2.9 | 91.2 | 17.2 |

Acute Toxicity

Each of the test compounds were suspended in aqueous gum arabicum and the suspension was administered orally to ddy male mice having a body weight of 22 to 26 g. $LD_{50}$ was calculated by the Behrens-Kärber method [Arch. exp. Path. Pharmak., 177, 379 (1935)] from the mortality one week after administration. The results obtained are shown in Table 4 below.

TABLE 4

| Test Compound | $LD_{50}$ (mg/kg) |
|---|---|
| Compound C | 1450 |
| Compound D | 2000 |
| Compound E | 2000 |
| Compound F | 465 |
| Compound H | 550 |

As is apparent from the results shown in Table 4, the compounds of this invention (Compounds C to E) exhibited acute toxicity lower than those of the known compounds (Compounds F and H) and, therefore, possess a very high safety margin.

Stability to Light 50 mg of each of the test compounds was placed in a quartz dish and exposed to sun light for the periods shown in Table 5 below (total, for 8 hours), and changes in appearance of the exposed test compound was observed visually. The results obtained are shown in Table 5 below.

As is apparent from the results, the comparative Compound F and Compound H (nifedipine) showed slight color changes even after 5 minutes' exposure and also showed marked changes thereafter, whereas the compounds of this invention (Compounds A, C, D and E) did not show any changes even after exposure for a total of 8 hours, indicating that the compounds of this invention are very stable to light.

TABLE 5

| Compound | Light-Exposure Time | | | | |
|---|---|---|---|---|---|
| | 5 min. | 1 hour | 2 hours | 3 hours | 8 hours |
| Compound A | (−)* | (−) | (−) | (−) | (−) |
| Compound C | (−) | (−) | (−) | (−) | (−) |
| Compound D | (−) | (−) | (−) | (−) | (−) |
| Compound E | (−) | (−) | (−) | (−) | (−) |
| Compound F | Slight color change | Slight color change, marked solubilizing | Marked color change, marked solubilizing | | |
| Compound H | Slight color change | Marked color change | Marked color change, slight solubilizing | Marked color change, marked solubilizing | |

Note:
*(−): No change.

PREPARATION EXAMPLES

Capsules

Capsules each containing the following formulation was prepared in a conventional manner.

| | |
|---|---|
| Compound C | 2.5 mg |
| Glycerin | 10 mg |
| Polyethylene glycol | 160 mg |
| Water | 16.5 mg |
| Total | 189 mg |

Tablets

Tablets each containing the following formulation was prepared in a conventional manner.

| | |
|---|---|
| Compound A | 10 mg |
| Lactose | 102.5 mg |
| Starch | 27 mg |
| Crystalline Cellulose | 27 mg |
| Polyvinyl pyrrolidone | 12 mg |
| Polysolvate | 0.6 mg |
| Water | 40 mg |
| Magnesium Stearate | 0.9 mg |
| Total | 220 mg |

Granules

Granules having the following formulation was prepared in a conventional manner and filled in usual twin-shell capsules.

| | |
|---|---|
| Compound D | 5 mg |
| Lactose | 51 mg |
| Starch | 14 mg |
| Crystalline Cellulose | 14 mg |
| Polyvinyl pyrrolidone | 0.5 mg |
| Polysolvate | 20 mg |
| Water | 20 mg |
| Total | 110.5 mg/capsule |

What is claimed is:

1. A 1,4-dihydropyridine compound represented by the formula

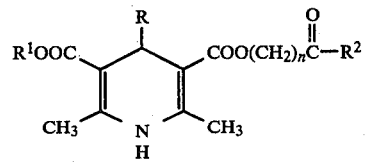

wherein R represents a 2- or 3-nitrophenyl group, $R^1$ represents a straight or branched chain alkyl group having 1 to 4 carbon atom, $R^2$ represents hydrogen or a methyl group, X represents an oxygen atom, an ethylenedioxy group, a propylenedioxy group, an ethylenedithio group, a propylenedithio group or an ethylene group, and n is an integer of 1 or 2.

2. A compound as claimed in claim 1, wherein R represents a 2- or 3-nitrophenyl group, $R^1$ represents a straight or branched chain alkyl group having 1 to 4 carbon atoms, $R^2$ represents a methyl group, X represents an ethylenedioxy group, and n is 1.

3. A compound as claimed in claim 1, wherein R represents a 2- or 3-nitrophenyl group, $R^1$ represents a straight or branched chain alkyl group having 1 to 4 carbon atoms, $R^2$ represents a methyl group, X represents an oxygen atom, and n is 1.

4. A compound as claimed in claim 1, wherein R represents a 2- or 3-nitrophenyl group, $R^1$ represents a straight or branched chain alkyl group having 1 to 4 carbon atoms, $R^2$ represents hydrogen, X represents an ethylene group and n is 1.

5. A compound as claimed in claim 2, wherein R represents a 3-nitrophenyl group, $R^1$ and $R^2$ each represents a methyl group, X represents an ethylenedioxy group and n is 1.

6. A compound as claimed in claim 3, wherein R represents a 2-nitrophenyl group, $R^1$ and $R^2$ each represents a methyl group, X represents an oxygen atom, and n is 1.

7. A compound as claimed in claim 4, wherein R represents a 3-nitrophenyl group, $R^1$ represents a methyl group, $R^2$ represents hydrogen, X represents an ethylene group and n is 1.

8. A compound as claimed in claim 4, wherein R represents a 3-nitrophenyl group, $R^1$ represents an ethyl group, $R^2$ represents hydrogen, X represents an ethylene group and n is 1.

9. A compound as claimed in claim 4, wherein R represents a 3-nitrophenyl group, $R^1$ represents a propyl group, $R^2$ represents hydrogen, X represents an ethylene group and n is 1.

* * * * *